United States Patent [19]

Seki et al.

[11] Patent Number: 5,635,491
[45] Date of Patent: Jun. 3, 1997

[54] LYOPHILIZED FATTY EMULSIONS AND A PROCESS FOR THE PRODUCTION THEREOF

[75] Inventors: Junzo Seki, Hyogo; Hirofumi Yamamoto, Kyoto; Shuji Yamane, Kyoto; Yutaka Takahashi, Kyoto; Kouichi Ushimaru, Kyoto, all of Japan

[73] Assignee: Nippon Shinyaku Co., Ltd., Japan

[21] Appl. No.: 50,216

[22] PCT Filed: Nov. 5, 1991

[86] PCT No.: PCT/JP91/01509

§ 371 Date: Jun. 21, 1993

§ 102(e) Date: Jun. 21, 1993

[87] PCT Pub. No.: WO92/07552

PCT Pub. Date: May 14, 1992

[30] Foreign Application Priority Data

Nov. 6, 1990 [JP] Japan ................... 2-301639
Nov. 6, 1990 [JP] Japan ................... 2-301640
Nov. 16, 1990 [JP] Japan ................... 2-312056

[51] Int. Cl.$^6$ .................. A61K 31/70; C07N 1/00
[52] U.S. Cl. ................................................ 514/53
[58] Field of Search ................ 514/53, 937, 938, 514/943; 252/312, 314; 424/172

[56] References Cited

U.S. PATENT DOCUMENTS

| 4,102,999 | 7/1978 | Umezawa et al. ............ 424/123 |
| 4,486,417 | 12/1984 | Sugimoto et al. ............ 425/180 |

FOREIGN PATENT DOCUMENTS

| 0134568 | 3/1985 | European Pat. Off. . |
| 0171084 | 2/1986 | European Pat. Off. . |
| 0211258 | 2/1987 | European Pat. Off. . |
| 211257 | 2/1987 | European Pat. Off. . |
| 315079 | 5/1989 | European Pat. Off. . |

OTHER PUBLICATIONS

Abstract of JP 60001123, Derwent Info Ltd.

*Primary Examiner*—Elli Peselev
*Attorney, Agent, or Firm*—Graham & James LLP

[57] ABSTRACT

A lyophilized preparation which releases a fat emulsion, wherein the emulsion particle has a mean diameter of 10 to 100 nm, when redissolved prior to use. This preparation is produced by adding maltose in an arbitrary stage of the production of said emulsion prior to lyophilization.

11 Claims, No Drawings

LYOPHILIZED FATTY EMULSIONS AND A PROCESS FOR THE PRODUCTION THEREOF

TECHNICAL FIELD

The present invention relates to a lyophilized preparation which is produced by lyophilization of a fatty emulsion composed of emulsion particles whose mean particle size is 10–100 nm.

BACKGROUND ART

Fatty emulsions composed of emulsion particles whose mean particle size is 10–100 nm are known to have effects such as improvement of distribution of drugs through the blood and movement thereof from their sites of application to the lesion tissues, and thus have excellent characteristics which have been hitherto unknown (Japanese Patent Application Disclosure HEI-2-203 etc.).

Generally, it is convenient for fatty emulsions to be preserved in a form readily preparable into emulsions just before their use.

Considering the possibility that the particle size of fatty emulsions changes with time, said fatty emulsions are preferred to be lyophilized preparations.

Also drugs in fatty emulsions are easily expected to be stable at low temperatures and in a dry state, which is an additional reason for the preference of lyophilized preparations.

Studies have long been made regarding techniques for lyophilization of emulsions. For example, liposomes different from the fatty emulsions of the present invention are disclosed in PCT Transfer Japanese Patent Application Disclosure SHO 62-501631, etc., while lyophilized preparations composed of oil in water types of emulsions are disclosed in Japanese Patent Application Disclosure SHO 60-224617, Japanese Patent Application Disclosure SHO 60-239417, etc., respectively. Lyophilization techniques for fatty emulsions with a particle size of 0.2 μm were studied from various points of view, and a remarkable increase in particle size was observed upon redissolution after drying. Moreover, addition of a surfactant, though its clinical safety has not been guaranteed, was tried, with no satisfactory effects.

Fatty emulsions are assembly of low molecular weight compounds in water, and their lyophilization while maintaining the assemby structure was difficult, We the present inventors have investigated lyophilized preparations of fatty emulsions made of emulsion particles having an mean particle size of 10 nm–100 nm, but this has resulted in major problems in such lyophilized preparations, e.g., the dried cakes are not uniform, are pasty or adhesive, and suffer from cracks, cut-outs, shrinkage and so on. Additional serious defects were that an increase in particle size was observed after redissolution and many emulsion particles that exceeded 100 nm in particle size were found.

For the production of lyophilized preparations of fatty emulsions, generally, the use of an aid has been attempted for lyophilization. Such an aid includes a monosaccharide such as glucose, a disaccharide such as trehalose, other saccharides such as sorbitol, starch, etc., an amino acid such as glycine, dextran, glycol or a derivative thereof (for example, Japanese Patent Application Disclosure SHO 62-29513).

Even with the use of these aids, however, lyophilized preparations of fatty emulsions composed of emulsion particles, which maintained the mean particle size of 10 nm–100 nm or the value observed prior to the lyophilization, could not be obtained.

DISCLOSURE OF THE INVENTION

We the present inventors have repeated earnest research to produce a lyophilized preparation of a fatty emulsion composed of emulsion particles which have an mean particle size of 10 nm–100 nm. As a result, we have accidentally found that incorporation of maltose during the production of a fatty emulsion settles the above-mentioned problems at a stroke, and thus the present invention has been completed.

Accordingly, the gist of the present invention resides in the incorporation of maltose during the production of lyophilized preparations of fatty emulsions composed of emulsion particles which have an mean particle size of 10 nm–100 nm, and therefore the present invention relates to the two: the production process and lyophilized preparations produced by the process.

Saccharides are usually used as aids for lyophilization, and other lyophilization aids of the prior art include, for example, amino acids, but, the effects of the present invention cannot be accomplished for lyophilization of fatty emulsions of emulsion particles which have an mean particle size of 10 nm–100 nm, even with the use of a saccharide other than maltose or any other aid for lyophilization. Glucose, trehalose, etc. are understood to produce somewhat satisfactory effects when the emulsion is redissolved immediately after lyophilization, but such effects are lost when the lyophilized product is subjected to accelerated heating. However, only maltose exhibited an apparent effect of resistance to such accelerated heating. This fact was first discovered by the present inventors.

Lyophilized preparations according to the present invention undergo little increase in particle size of the emulsion particles upon redissolution.

Lyophilized preparations of the present invention are made of dried cakes in a state completely identical to that just after lyophilization, and reconstruction thereof by the addition of water or the like does not cause any change in particle size of emulsion particles. Lyophilized preparations of the present invention keep their very excellent stability despite accelerated heating.

According to the present invention, maltose may be added in any step before lyophilization, during the production of a fatty emulsion according to the present invention. It may be mixed with a lipid prior to emulsification, or dissolved beforehand in water to be added for emulsification. It may be added during the process for emulsification. Maltose may be added to fatty emulsions immediately before lyophilization thereof.

The amount of maltose added according to the present invention is not particularly limited. Preferably it is 1–30% (w/v), and more preferably, 3–15% (w/v).

According to the present invention, maltose may be used very safely for medical treatment, for example, by intravenous administration, without any toxicity issues.

The temperature and the degree of reduction in pressure for the lyophilization process may be such as employed in the conventional process. They are desired to be controlled by the properties of the drug contained in the emulsion or the constituent lipid thereof. The lyophilized fatty emulsion according to the present invention may be readily redissolved upon addition of a desired appropriate solution. Generally, such a solution includes water for injection, and physiological saline and other infusions for general use may be employed as well. The quantity of the solution is preferred to be more than 0.5 times that of the preparation before lyophilization.

According to the present invention, absolutely no addition of a surfactant or solubilizer nor heating is required.

This is an additional excellent effect of the present invention.

The lyophilized preparations according to the present invention are very stable, and may be present in a stable state even during storage at room temperature, with their appearance remaining almost unchanged even after storage at room temperature for more than one year, and the solubility and the particle size of the emulsion particles not influenced upon addition of water or the like.

As mentioned above, the emulsion particles with an mean particle size being 10 nm to 100 nm, which compose the fatty emulsion according to the present invention may be kept from being incorporated into the reticuloendothelial system (RES) These very fine emulsion particles maintain a higher blood concentration than fatty emulsions of a diameter being approximately 0.2 μ and are capable of leaking out without difficulties from blood vessels via sites with increased vascular permeability. Blood vessels are said to contain various sites called pore systems (pore systems: small pore systems exist with a diameter of up to 9 nm and large pore systems exist with a diameter of 25-70 nm, while the permeability is known to increase at various lesion sites including tumor neovascularity.) and other intercellular spaces, and the vascular permeability progresses at various lesion sites suffering from inflammation, tumor, atheroma, etc., in which sites many very fine emulsion particles leak out selectively from blood vessels via the pore systems mentioned above and migrate inside the lesion tissues. At the same time, the drug included in these particles migrates inside the lesion sites as well. Thus, the drug moves to the lesion sites easily and selectively, at which sites the drug concentration increases, thereby multiplying the effects thereof. On the other hand, the permeability of particles of 10nm or smaller is poor for normal cells due to the presence of the pore systems mentioned above, which prevents the movement of such fine particles form blood vessels to normal cells. Considering the above-mentioned, it is apparent that fatty emulsions with an mean particle size of approximately 10 nm to 70 nm, and more particularly, when acceptable pore size of the pore systems and the particle distribution pattern of the fatty emulsion particles are considered, fatty emulsions with an mean particle size of about 10–100 nm, are the best for the improvement of the drug migration (see Japanese Patent Application Disclosure HEI 2-203).

The lipids available for use in the fatty emulsions according to the present invention include simple lipids from natural animals, plants or minerals, derived lipids, compound lipids and mixtures thereof. Specifically, they include lipids listed in the examples as well as, for example, various lipids described in Japanese Patent Application Disclosure HEI 2-203.

Even drugs, which have been incapable of being administered due to their instability in the body, may be easily administered by the use of the lyophilized preparations according to the present invention. The drugs treated according to the present invention are present in oil drops of lipids, in a state intercepted from the surroundings, so their enzymatic or nonenzymatic decomposition may be prevented.

The drug to which a lyophilized preparation according to the present invention may be applied is not particularly limited. It may be, for example, an antiinflammatory agent, analgesic, antiallergic agent, antibiotic, chemotherapeutic, antitumor agent, antiviral agent, anti-arteriosclerotic agent. hypolipidemic agent, antiulcer agent, immunomodulator, vaccine. radical scavenger, bronchodilator, soporific, tranquilizer, local anesthetic, fat-soluble vitamin, diagnostic reagent, etc. Examples thereof include, for example, mitomycin C derivatives such as ancitabine, fluorouracil, mitomycin C, mitomycin C farnesylamide, nonyloxycarbonylmitomycin C, cholestearyloxyglycylmitomycin C, mitomycin C farnesylacetamide, etc., cytarabine derivatives such as carmofur, futraful palmitate, 5-fluorouracil myristate, adriamycin, daunomycin, aclarubicin hydrochloride, maclarubicin, vinblastine, vincristin, fatty acid esters of cytarabine, etc., antitumor agents such as mitotane, estramustine, etc., antiviral agents such as dichloroflaban, etc., steroids, for example, dexamethasone palmitate, hydrocortisone palmitate, prednisolone palmitate, dexamethasone stearate, methylprednisolone, paramethasone, fluocinolone acetonide, betamethasone propionate, fatty acid esters of hydrocortisone, aldosterone, spironolactone, etc., and nonsteroids, for example, ibuprofen, flufenamic acid, ketoprofen, phenacetin, antipyrine, aminopyrine, phenylbutazone indolacetate, biphenylylpropionic acid derivatives, indomethacin, ethoxycarbonyl methyl ester of indomethacin, stearyl ester of indomethacin, gold cetyl thiomalate, diclofenac, acetylsalicylic acid and derivatives thereof, Antiallergic agents such as tranilast, ketotifen, azelastin, etc. may also be used. The antibiotics and chemotherapeutics available for use include tetracycline, erythromycin, midecamycin, amphotericin B and related compounds, minocycline, miconazole, etc. Examples of prostaglandins include $PGE_1$, $PGA_1$, alkyl esters of $PGA_1$, alkyl esters of $PGE_1$. $PGE_1$ derivatives, $PGI_2$ derivatives, PGD derivatives, etc. Antihistamines such as diphenhydramine, orphenadirin, chlorphenoxamine, chlorphenilamine, promethazine, meclizine, cyproheptadine, roxatidine acetate, etc. may be mentioned. Also, local anesthetics such as lidocaine, benzocaine, dantrolene, cocaine, tetracaine, piperocaine, mepivacaine, etc. or their derivatives may be mentioned. Hepatotherapeutic agents, for example, malotilate, glycyrrhetinic acid, ethyl acetylglycyrrhetinate, methyl glycyrrhetinate, etc. or antiulcer agents, for examples farnesol, geraniol, gefarnate, teprenone, plaunotol, sofaicone, etc. may be mentioned. Central nervous system agents, for example, phenobarbitol, methaqualone, heroin, diazepam, medazepam, prazepam, clotiazepam, etizolam, meclizine, buclizine, adiphenine, metamphetamine, imipramine, chlorimipramine, amitriptyline, mianserin, trimethadione, phensuximide, tetrabenzamide, benzquinamide, camphor, dimorphoramine, strychnine, chlorpromazine, promethazine, prochlorperazine, mequitazine, triflupromazine, levomepromazine, difenidol, etc. or their derivatives may be mentioned.

As the bronchodilators, there may be mentioned bestphyline and other theophylline derivatives, methylephedrine, etc. Also mentioned are cholinergic blocking agents, for example, benztropine, physostigmine, atropine, scopolamine etc.; cholinergic blockers, for example, oxyphencyclimine, pirenzepine, etomidoline, etc.; calcium blockers, for example, diltiazem, nifedipine, verapamil, etc.; blockers, for example, dibenzamine, phenoxybenzamine, etc.; antitussives, for example, noscapine, dextromethorphan, pentoxyverine, benproperine, etc.; therapeutic agents for prostate hyperplasia, for example, gastrone, oxendolone, etc.; therapeutic agents for glaucoma, for example, pilocarpine, etc.; smooth muscle active drugs, for example, sparteine, papaverine, etc.; therapeutic agents for hyperlipidemia, for example, clofibrate, simfibrate, probucol, etc. Additional examples thereof includes, for example, amino acids, vitamins, dilazep hydrochloride, ubidecarenone, flavoxate, cyclosporin A, vaccines such as influenza vaccine, dibenzthione, diphenylpyraline, phenovalin, methadione, tofisopam, limonene, etc. The fat-soluble vitamins include vitamin A and derivatives thereof, vitamin E and derivatives thereof, K vitamins and derivatives thereof, D vitamins and derivatives thereof, etc.

Additional embodiments include guaiazulene and essential oils from crude drugs such as, for example, pricot kernel oil, fennel oil, thyme oil, turpentine oil, eucalyptus oil, palm oil, poppy oil, camellia oil as well.

The diagnostic reagents include, for example, compounds labelled with radioisotopes, radioactive medicines, iodized poppy oil fat acid esters or iodine X contrast media, etc.

The drugs to which the present invention is applicable are not particularly limited, although those drugs for inflammation or tumors or related with blood vessel or immune system are commonly desired, in light of the properties of the fatty emulsions which are due to the particle size of the emulsions.

The drug concentration of the emulsion according to present invention may be adjusted appropriately based on the biological activity of the drug. In addition, appropriate adjust ent may be made as desired of the concentrations of the emulsion constituents in the emulsion preparation of the present invention and of the drug.

For the production of a lyophilized preparation according to the present invention, various processes of the prior art for the production of fatty emulsions may be utilized in order to produce the fatty emulsions according to the present invention. For example, they may be produced by a process where all the constituents including the drug are fully emulsified with a Manton-Gauline homogenizer, microfluidizer, ultrasonic homogenizer or the like, or a process wherein the constituents are made soluble by a surfactant (e.g., bile acid), a water-soluble solvent (e.g., ethanol, polyethylene glycol) or the like, and then the surfactant, water-soluble solvent, etc. are removed by dialysis, gel filtration, etc. Here, a fatty acid or a derivative thereof may be added as an emulsification aid. And they may be prodused by adding the drug to fatty emulsions that were prepared before hand as described above.

The shape and particle size of the fatty emulsion of the present invention may be easily confirmed with an electron microscope, light-scattering particle size analyzer, membrane filter, etc.

The fatty emulsions according to the present invention may contain as desired additives and aids commonly used in injections. For example, examples thereof include antioxidants, antiseptics, stabilizers, isotonizing agents, buffers, etc. The required and optimum amounts of these substances may be varied depending on the object.

The general procedures which are already publicly known may be applicable to lyophilization of the fatty emulsions of the present invention which contain maltose. As an example, the fatty emulsion is packaged in 20 ml glass vials (hight of the solution in a vial: approx. 15 mm). These are lyophilized according to a program for the increase in the temperature from −40° to 30° C. over a period of about 15 hours (the degree of vacuum: approx. 0.02 torr). The contents of the vials are replaced by nitrogen gas, and the vials are capped for the completion of the production of the lyophilized preparations.

THE BEST MODE FOR CARRYING OUT THE INVENTION

A more detailed explanation will be made hereunder regarding the present invention, with reference to the Examples and test results relating to the production of lyophilized preparations according to the present invention.

EXAMPLE 1

3 g of dexamethasone palmitate, 50 g of refined soy bean oil and 20 g of refined egg yolk lecithin were mixed while heating at approximately 60° C., after which 500 ml of an aqueous solution of maltose, which contains 10% maltose, was added as a lyophilization aid to the mixture which was stirred with a homomixer to prepare a crude emulsion solution. The crude emulsion solution was subjected to emulsification under pressure with a Manton-Gauline homogenizer to prepare an emulsion comprising emulsion particles having a particle size of 10–100 nm. This was lyophilized in a conventional manner.

The state of the dried cake was very favorable, with no cutting-out or shrinkage observed. And, upon addition thereto of water for injection for redissolution thereof, the dissolution reached completeness very rapidly, without any change being found in the particle size of the emulsion particles found after dissolution, thus resulting in a complete reconstitution.

EXAMPLE 2

30 mg of nifedipine, 0.6 g of refined soy bean oil and 0.5 g of refined egg yolk lecithin were mixed and dissolved in 100 ml of a mixture solution of chloroform/methanol (1/1, v/v), after which the solvent was completely removed with a rotary evaporator under reduced pressure. To the mixture was added 8 ml of a 5% aqueous solution of maltose, followed by stirring with a homogenizer to prepare a crude emulsion solution. Then, additional amount of a 5% aqueous solution of maltose was added to a constant volume of 10 ml, after which the mixture was subjected to emulsification with an ultrasonic homogenizer (Branson Model 185) for 60 minutes, while cooling on ice, to prepare an emulsion comprising emulsion particles having a particle size of 10–100 nm. This was lyophilized in a conventional manner. The state of the dried cake was very favorable, with no cutting-out or shrinkage observed. And, upon addition thereto of water for injection for redissolution thereof, dissolution reached completeness very rapidly, without any change being found in the particle size of the emulsion particles after dissolution thus resulting in a complete reconstitution.

EXAMPLE 3

30 mg of amphotericin B, 5 g of refined soy bean oil and 5 g of refined egg yolk lecithin were kneaded to homogenization using mortar, followed by addition of 10 g of maltose for further kneading. To the solution was added 80 ml of water for injection, and the mixture was stirred with a Polytron homogenizer to prepare a crude emulsion solution. Then, an additional amount of water for injection was added to a constant volume of 100 ml, after which the mixture was subjected to emulsification with a multifluidizer while cooling on ice, to prepare an emulsion comprising emulsion particles having a particle size of 10–100 nm. This was lyophilized in a conventional manner. The state of the dried cake was very favorable, with no abominable cracking, cutting-out or shrinkage observed. And, upon addition thereto of water for injection for redissolution thereof, dissolution reached completeness very rapidly, without any change being found in the particle size of the emulsion particles after dissolution, thus resulting in a complete reconstitution.

EXAMPLE 4

2 g of miconazole, 20 g of refined soy bean oil and 30 g of refined egg yolk lecithin were heated to mixture at 60° C., after which a 20% aqueous solution of maltose was added thereto to a constant volume of 100 ml, after which the mixture was subjected to emulsification with a homogenizer to prepare a crude emulsion solution. This crude emulsion solution was emulsified with a microfluidizer under pressure to prepare an emulsion comprising emulsion particles having a particle size of 10–100 nm. This was lyophilized in a conventional manner. The state of the dried cake was very favorable, with no cutting-out or shrinkage observed. And, upon addition thereto of water for injection for redissolution thereof, dissolution reached completeness very rapidly, without any change being found in the particle size of the emulsion particles after dissolution, thus resulting in a complete reconstitution.

EXAMPLE 5

1 mg of cyclosporin A, 0.5 g of cholesteryl oleate and 0.5 g of refined egg yolk lecithin were mixed and dissolved in 10 ml of a mixture solution of chloroform/methanol (1/1, v/v). after which the solvent was completely removed with a rotary evaporator under reduced pressure. To the mixture was added 8 ml of a 5% aqueous solution of maltose, followed by stirring with a homogenizer to prepare a crude emulsion solution. Then additional amount of a 5% aqueous solution of maltose was added to a constant volume of 100 ml, after which the mixture was subjected to emulsification with an ultrasonic homogenizer (Branson Model 185) for 60 minutes, to prepare an emulsion comprising emulsion particles having a particle size of 10–100 nm. This was lyophilized in a conventional manner. The state of the dried cake was very favorable, with no cutting-out or shrinkage observed. And, upon addition thereto of water for injection for redissolution thereof, dissolution reached completeness very rapidly, without any change being found in the particle size of the emulsion particles after dissolution, thus resulting in a complete reconstitution.

EXAMPLE 6

3 mg of amphotericin B, 0.5 g of refined soy bean oil, 0.4 g of refined egg yolk lecithin and 0.1 g of dimyristoylphosphatidylglycerol were mixed and dissolved in 100 ml of a mixture solution of chloroform/methanol (1/1, v/v). after which the solvent was completely removed with a rotary evaporator under reduced pressure. To the mixture was added 8 ml of 0.1% saline, followed by stirring with a homogenizer to prepare a crude emulsion solution. The mixture was subjected to emulsification with an ultrasonic homogenizer (Branson Model 185) for 60 minutes, to prepare an emulsion comprising emulsion particles having a particle size of 10–100 nm. To this was added 1 g of maltose for dissolution, and then water added thereto to a constant volume of 10 ml. This was lyophilized in a conventional manner. The state of the dried cake was very favorable, with no cracking, cutting-out or shrinkage observed. And, upon addition thereto of water for injection for redissolution thereof, dissolution reached completeness very rapidly, without any change being found in the particle size of the emulsion particles after dissolution thus resulting in a complete reconstitution.

EXAMPLE 7

3 mg of nonyloxycarbonylmitomycin C, 0.5 g of refined soy bean oil, 0.4 g of hydrogenated egg yolk lecithin and 0.1 g of cholesterol were mixed and dissolved in 100 ml of a mixture solution of chloroform/methanol (1/1, v/v), after which the solvent was completely removed with a rotary evaporator under reduced pressure. To the mixture was added 5 ml of a 20% aqueous solution of maltose, followed by stirring with a homogenizer to prepare a crude emulsion solution. Then, an additional amount of a 20% aqueous solution of maltose was added to a constant volume of 10 ml, after which the mixture was subjected to emulsification with an ultrasonic homogenizer (Branson Model 185) for 60 minutes to prepare an emulsion comprising emulsion particles having a particle size of 10–100 nm. This was lyophilized in a conventional manner. The state of the dried cake was very favorable, with no cutting-out or shrinkage observed. And, upon addition thereto of water for injection for redissolution thereof, dissolution reached completeness very rapidly, without any change being found in the particle size of the emulsion particles after dissolution, thus resulting in a complete reconstitution.

EXAMPLE 8

3 g of dexamethasone palmitate and 20 g of refined egg yolk lecithin were mixed and kneaded, after which 500 ml of an aqueous solution of maltose, which contains 10% maltose, was added as a lyphilization aid to the mixture which was stirred with a homomixer to prepare a crude emulsion solution. The crude emulsion solution was subjected to emulsification under pressure with a Manton-Gauline homogenizer to prepare an emulsion comprising emulsion particles having a particle size of 10–100 nm. This was lyophilized in a conventional manner.

The state of the dried cake was very favorable, with no cutting-out or shrinkage observed. And, upon addition thereto of water for injection for redissolution thereof, the dissolution reached completeness very rapidly, without any change being found in the particle size of the emulsion particles found after dissolution, thus resulting in a complete reconstitution.

Results of the Tests

Fatty emulsions with an mean particle size of 35 nm, which were prepared using water for injection and contained 5% refined soy bean oil and 5% refined egg yolk lecithin, were completely dissolved by the addition of various additives listed below, and then lyophilized in a conventional manner. Hereunder were noted the states of the lyophilized cakes immediately after production and after subjection to accelerated heating or storage at 40° C. for 1 month, solubility observed upon addition of water for injection, and the results of the measurement of the particles sizes.

Maltose (10%)

(Immediately after production)

Appearance: Very good. No cracking, cutting-out, shrinkage, adhesion, or undissolved lumps.

Solubility: Completely dissolved (reconstituted) by shaking by hand for several seconds.

Mean particle size: 35 nm (no change)

(After accelerated heating)

Appearance: Very good. No cracking, cutting-out, shrinkage, adhesion, or undissolved lumps.

Solubility: Completely dissolved (reconstituted) by shaking by hand for several seconds.

Mean particle size: 35 nm (no change)

Sucrose (10%)

(Immediately after production)

Appearance: Acceptably good, and no shrinkage, adhesion or the like observed.

Solubility: Completely dissolved (reconstituted) by shaking by hand for twenty or thirty seconds.

Mean particle size: 40 nm (no significant change)

(After accelerated heating)

Appearance: A little shrinkage.
Solubility: Poor. The solution was turbid.
Mean particle size: Not less than 200 nm.
  Trehalose (10%)
  (Immediately after production)
Appearance: Acceptably good, and no shrinkage, adhesion or the like observed.
Solubility: Completely dissolved (reconstituted) by shaking by hand for twenty or thirty seconds.
Mean particle size: 38 nm (no significant change)
  (After accelerated heating)
Appearance: A little shrinkage.
Solubility: A little poor. Dissolved by shaking by hand for several minutes. The solution was turbid.
Mean particle size: 160–180 nm.
  Lactose (10%)
  (Immediately after production)
Appearance: Acceptably good, and no shrinkage, adhesion or the like observed.
Solubility: Not completely dissolved even by shaking by hand for twenty or thirty minutes. The solution was significantly turbid.
Mean particle size: Not less than 200 nm.
  Glucose (5%)
  (Immediately after production)
Appearance: Acceptably good, and no shrinkage, adhesion or the like observed.
Solubility: Completely dissolved (reconstituted) by shaking by hand for twenty or thirty minutes.
Mean particle size: 42 nm (no significant change)
  (After accelerated heating)
Appearance: Significant shrinkage and adhesion.
Solubility: Dissolved by shaking by hand for several minutes. The solution was turbid.
Mean particle size: Not less than 200 nm.
  Mannitol (5%)
  (Immediately after production)
Appearance: Shrinkage and cracking observed.
Solubility: Not completely dissolved even by shaking by hand for twenty or thirty minutes. The solution was significantly turbid.
Mean particle size: Not less than 200 nm.
  Fructose (5%)
  (Immediately after production)
Appearance: Shrinkage and cracking observed.
Solubility: Not completely dissolved even by shaking by hand for twenty or thirty minutes. The solution was significantly turbid.
Mean particle size: Not less than 200 nm.
  Sorbitol (5%)
  (Immediately after production)
Appearance: Significant shrinkage, cracking and adhesion observed.
Solubility: Not completely dissolved even by shaking by hand for twenty or thirty minutes. The solution was significantly turbid.
Mean particle size: Unmeasurable (Noteworthy enlargement).
  L-arginine (2%)
  (Immediately after production)
Appearance: Acceptably good, and no shrinkage, adhesion or the like observed.
Solubility: Not completely dissolved even by shaking by hand for twenty or thirty minutes. The solution was significantly turbid.
Mean particle size: Not less than 200 nm.
  L-proline (2%)
  (Immediately after production)
Appearance: Shrinkage and cracking observed.
Solubility: Not completely dissolved even by shaking by hand for twenty or thirty minutes. The solution was significantly turbid.
Mean particle size: Not less than 200 nm.
  Glycine (2%)
  (Immediately after production)
Appearance: Significant shrinkage, cracking and adhesion observed.
Solubility: Not completely dissolved even by shaking by hand for twenty or thirty minutes. The solution was significantly turbid.
Mean particle size: Not less than 200 nm.
  DL-valine (2%)
  (Immediately after production)
Appearance: Acceptably good, and no shrinkage, adhesion or the like observed.
Solubility: Not completely dissolved even by shaking by hand for twenty or thirty minutes. The solution was significantly turbid.
Mean particle size: Not less than 200 nm.
  DL-alanine (2%)
  (Immediately after production)
Appearance: Acceptably good, and no shrinkage, adhesion or the like observed.
Solubility: Not completely dissolved even by shaking by hand for twenty or thirty minutes. The solution was significantly turbid.
Mean particle size: Not less than 200 nm.
  DL-asparagine (2%)
  (Immediately after production)
Appearance: Acceptably good, and no shrinkage, adhesion or the like observed.
Solubility: Not completely dissolved even by shaking by hand for twenty or thirty minutes. The solution was significantly turbid.
Mean particle size: Not less than 200 nm.
  Low molecular weight dextran (0.5%)
  (Immediately after production)
Appearance: Acceptably good, and no shrinkage, adhesion or the like observed.
Solubility: Not completely dissolved even by shaking by hand for twenty or thirty minutes. The solution was significantly turbid.
Mean particle size: Unmeasurable (Noteworthy enlargement).
  High molecular weight dextran (0.5%)
  (Immediately after production)
Appearance: Acceptably good, and no shrinkage, adhesion or the like observed.
Solubility: Not completely dissolved even by shaking by hand for twenty or thirty minutes. The solution was significantly turbid.
Mean particle size: Unmeasurable (Noteworthy enlargement).
  Polyethylene glycol 6000 (1%)
Appearance: Significant shrinkage, cracking and adhesion observed.
Solubility: Not completely dissolved even by shaking by hand for twenty or thirty minutes. The hand for twenty or thirty seconds. The solution was significantly turbid.
Mean particle size: Unmeasurable (Noteworthy enlargement).
  Starch (1%)
Appearance: Acceptably good, and no shrinkage, adhesion or the like observed.

Solubility: Not completely dissolved even by shaking by hand for twenty or thirty minutes. The solution was significantly turbid.
Mean particle size: Unmeasurable (Noteworthy enlargement).

Hydroxypropylcellulose (1%)
Appearance: Significant shrinkage, cracking and adhesion observed.
Solubility: Not completely dissolved even by shaking by hand for twenty or thirty minutes. The solution was significantly turbid.
Mean particle size: Unmeasurable (Noteworthy enlargement).

Polyvinylpyrrolidone (1%)
Appearance: Significant shrinkage, cracking and adhesion observed.
Solubility: Not completely dissolved even by shaking by hand for twenty or thirty minutes. The solution was significantly turbid.
Mean particle size: Unmeasurable (Noteworthy enlargement).

Albumin (1%)
Appearance: Acceptably good, and no shrinkage, adhesion or the like observed.
Solubility: Not completely dissolved even by shaking by hand for twenty or thirty minutes. The solution was significantly turbid.
Mean particle size: Unmeasurable (Noteworthy enlargement).

Hydroxypropylmethylcellulose (1%)
Appearance: Significant shrinkage, cracking and adhesion observed.
Solubility: Not completely dissolved even by shaking by hand for twenty or thirty minutes. The solution was significantly turbid.
Mean particle size: Unmeasurable (Noteworthy enlargement).

Methylcellulose (1%)
Appearance: Significant shrinkage, cracking and adhesion observed.
Solubility: Not completely dissolved even by shaking by hand for twenty or thirty minutes. The solution was significantly turbid.
Mean particle size: Unmeasurable (Noteworthy enlargement).

Carboxymethylcellulose sodium (1%)
Appearance: Acceptably good, and no shrinkage, adhesion or the like observed.
Solubility: Not completely dissolved even by shaking by hand for twenty or thirty minutes. The solution was significantly turbid.
Mean particle size: Unmeasurable (Noteworthy enlargement).

Polyvinyl alcohol (1%)
Appearance: Significant shrinkage, cracking and adhesion observed.
Solubility: Not completely dissolved even by shaking by hand for twenty or thirty minutes. The solution was significantly turbid.
Mean particle size: Unmeasurable (Noteworthy enlargement).

Glycerine (0.24M)
Appearance: Significant shrinkage, pasty,
Solubility: Not completely dissolved even by shaking by hand for twenty or thirty minutes. The solution was significantly turbid.
Mean particle size: Unmeasurable (Noteworthy enlargement).

Sodium chloride (0.15M)
Appearance: Significant shrinkage, pasty.
Solubility: Not completely dissolved even by shaking by hand for twenty or thirty minutes. The solution was significantly turbid.
Mean particle size: Unmeasurable (Noteworthy enlargement).

We claim:

1. A stable lyophilized composition, capable of reconstituting a fatty emulsion in which the mean particle size is 10–100 nm without substantial enlargement of the particle size between prior to lyophilization and after reconstitution with water, which comprises lyophilized lipid emulsion particles for a fatty emulsion wherein said particles comprise a therapeutically effective amount of a therapeutic active substance or a diagnostically effective amount of a diagnostic agent and an amount of maltose effective, upon dispersion of said lyophilized composition in water, to produce a fatty emulsion in which the mean emulsion particle size is 10–100 nm, without substantial enlargement of the particle size between prior to lyophilization add after reconstitution with water, under conditions of storage at elevated temperatures up to 40° C. or the accelerated heating equivalent thereof.

2. A lyophilized composition according to claim 1 which is produced by lyophilization of a fatty emulsion comprising lipid emulsion particles having a mean particle size of 10–100 nm, wherein said particles comprise said therapeutically effective amount of said therapeutic active substance or said diagnostically effective amount of said diagnostic agent, and said maltose wherein the concentration of maltose is 1–30% w/v of said fatty emulsion.

3. A lyophilized composition according to claim 2, wherein the concentration of maltose is 3–15% w/v of said fatty emulsion.

4. A lyophilized composition according to claim 1 which contains a therapeutically effective amount of an anti-inflammatory agent, an anti-tumor agent, an antibiotic agent, a chemotherapeutic agent or a therapeutic agent having an effect on the blood vessels or immune system of a human or animal.

5. A process for producing a lyophilized fatty emulsion capable of reconstituting a fatty emulsion in which the mean particle size is 10–100nm without substantial enlargement of the particle size between prior to lyophilization and after reconstitution with water, which comprises lyophilizing a fatty emulsion which comprises emulsion particles having a mean particle size of 10–100 nm wherein said particles comprise a therapeutically active substance or a diagnostic agent, and adding to the emulsion prior to lyophilization an amount of maltose effective, upon dispersion of said lyophilized composition in water, to produce a fatty emulsion in which the mean emulsion particle size is 10–100 nm, without substantial enlargement of the particle size between prior to lyophilization and after reconstitution with water, under conditions of storage at elevated temperatures up to 40° C. or the accelerated heating equivalent thereof.

6. A process according to claim 5 wherein the concentration of maltose is 1–30% w/v.

7. A process according to claim 6 wherein the concentration of maltose is 3–15% w/v.

8. A method of producing a pharmaceutical composition in the form of a fatty emulsion useful for administration to humans and animals which comprises adding water to the stable lyophilized composition according to claim 1 sufficient to form said fatty emulsion in which the mean emulsion particle size is 10–100 nm, without substantial enlargement of the particle size between prior to lyophilization and after reconstitution with water, under conditions of storage at elevated temperatures up to 40° C. or the accelerated heating equivalent thereof.

9. A method of producing a pharmaceutical composition in the form of a fatty emulsion useful for administration to humans and animals which comprises adding water to the stable lyophilized composition according to claim 2 sufficient to form said fatty emulsion in which the mean emulsion particle size is 10–100 nm, without substantial enlargement of the particle size between prior to lyophilization and after reconstitution with water, under conditions of storage at elevated temperatures up to 40° C. or the accelerated heating equivalent thereof.

10. A method of producing a pharmaceutical composition in the form of a fatty emulsion useful for administration to humans and animals which comprises adding water to the stable lyophilized composition according to claim 3 sufficient to form said fatty emulsion in which the mean emulsion particle size is 10–100 nm, without substantial enlargement of the particle size between prior to lyophilization and after reconstitution with water, under conditions of storage at elevated temperatures up to 40° C. or the accelerated heating equivalent thereof.

11. A method of producing a pharmaceutical composition useful for administration to humans and animals which comprises adding water to the stable lyophilized composition according to claim 4 sufficient to form said fatty emulsion in which the mean emulsion particle size is 10–100 nm, without substantial enlargement of the particle size between prior to lyophilization and after reconstitution with water, under conditions of storage at elevated temperatures up to 40° C. or the accelerated heating equivalent thereof.

* * * * *